(12) United States Patent
Woodward et al.

(10) Patent No.: US 9,700,338 B2
(45) Date of Patent: Jul. 11, 2017

(54) SMOOTH MOVEMENT SAFETY KNIFE SYSTEM AND METHOD

(71) Applicant: Surgistar, Inc., Vista, CA (US)

(72) Inventors: Jonathan Woodward, Vista, CA (US); Payal Goel, Vista, CA (US)

(73) Assignee: Surgistar, Inc., San Diego, CA (US)

( * ) Notice: Subject to any disclaimer, the term of this patent is extended or adjusted under 35 U.S.C. 154(b) by 0 days.

(21) Appl. No.: 14/803,807

(22) Filed: Jul. 20, 2015

(65) Prior Publication Data

US 2017/0020544 A1 Jan. 26, 2017

(51) Int. Cl.
| | | |
|---|---|---|
| *A61B 17/32* | (2006.01) | |
| *B29C 33/62* | (2006.01) | |
| *B29C 33/64* | (2006.01) | |
| *B29K 81/00* | (2006.01) | |
| *B29L 31/28* | (2006.01) | |
| *B29L 31/00* | (2006.01) | |
| *A61B 17/00* | (2006.01) | |
| *A61B 17/3211* | (2006.01) | |

(52) U.S. Cl.
CPC .............. *A61B 17/32* (2013.01); *B29C 33/62* (2013.01); *B29C 33/64* (2013.01); *A61B 2017/00526* (2013.01); *A61B 2017/00845* (2013.01); *A61B 2017/32113* (2013.01); *B29K 2081/06* (2013.01); *B29L 2031/286* (2013.01); *B29L 2031/7546* (2013.01)

(58) Field of Classification Search
CPC .......... A61B 17/32; A61B 2017/00526; B29C 33/64; B29C 33/62; B29L 2031/286; B29L 2031/7546; B29K 2081/06
See application file for complete search history.

(56) References Cited

U.S. PATENT DOCUMENTS 3,356,130 A * 12/1967 Mellen, Jr. ................ B28B 1/24
164/306
2015/0218354 A1* 8/2015 Kulshrestha ............ A61L 29/04
264/234

* cited by examiner

*Primary Examiner* — Richard Chang
(74) *Attorney, Agent, or Firm* — Mintz Levin Cohn Ferris Glovsky and Popeo, P.C.

(57) ABSTRACT

A medical scalpel system includes a safety handle and an internal mechanism that permits a blade to be extended and retracted relative to the safety handle. At least a portion of the system is manufactured pursuant to a process wherein a material, such as silicone or Teflon, is used in the manufacturing of the components to provide a smooth movement between components of an extension and retraction mechanism.

12 Claims, 3 Drawing Sheets

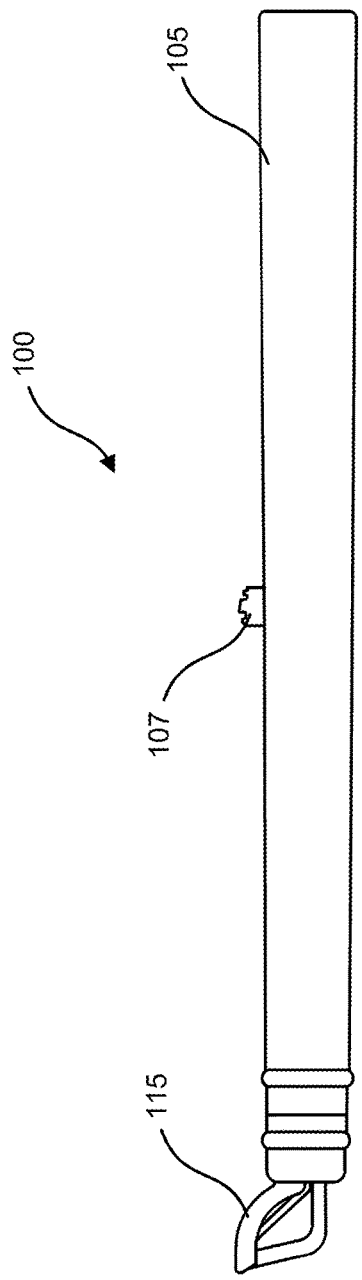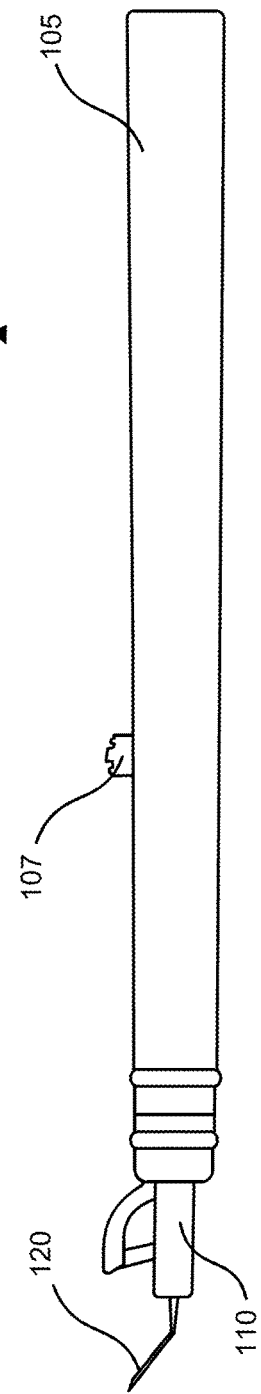

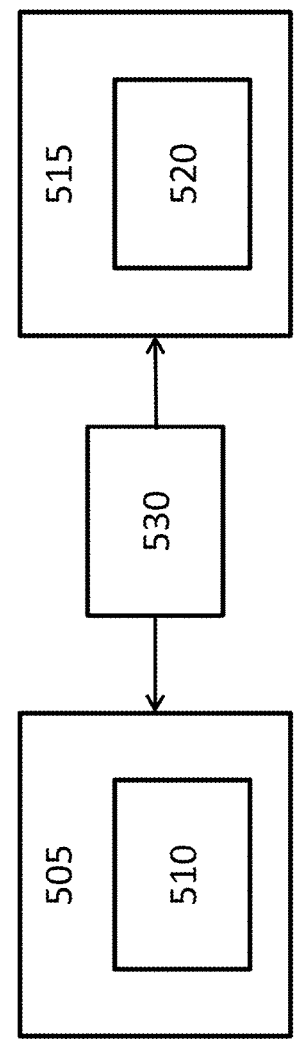

SMOOTH MOVEMENT SAFETY KNIFE SYSTEM AND METHOD

BACKGROUND

Surgical blade systems often have a safety feature that permits the blade to be transitioned between a retracted and an extended position. In the retracted position, the blade is contained within a handle or a sheath that prevents the blade from accidentally contacting or cutting a user. In the extended position, the blade extends outwardly from the handle such that it can be used to cut tissue.

Such systems include moving parts that permit the play to transition between the retracted and the extended position. It is highly desirable that such moving parts easily and smoothly transition between the retracted and extended positions. In view of this, there is a need for methods of manufacturing surgical blade systems that smoothly transition between retracted and extended positions.

SUMMARY

Disclosed is a blade device, such as a medical scalpel system, that includes a safety handle and an internal mechanism that permits a blade to be extended and retracted relative to the safety handle. At least a portion of the system is manufactured pursuant to a process wherein a material, such as silicone or Teflon, is used in the manufacturing of the components to provide a smooth movement between components of the extension/retraction mechanism.

In one aspect, there is disclosed a method of manufacturing a blade device, comprising: providing a blade; injecting a first material into a first mold, the first mold having an internal cavity shaped into a handle of the blade; injecting a second material into a second mold, the second mold having an internal cavity shaped into an internal mechanism of the handle; inserting a lubricant into at least one of the first and the second mold in order to reduce a coefficient of friction of a material in the first or second mold; permitting the first and the second material to cool within the first mold and the second mold so as to form a handle and an internal mechanism; and assembling the internal mechanism to the handle and to the blade.

Other features and advantages should be apparent from the following description of various embodiments, which illustrate, by way of example, the principles of the disclosure.

BRIEF DESCRIPTION OF THE DRAWINGS

FIG. 1 shows a side view of a blade device in a retracted state.

FIG. 2 shows a side view of the blade device in an extended state.

FIG. 5 shoes a schematic representation of a first mold, second mold, and a lubricant.

DETAILED DESCRIPTION

Figure 3:
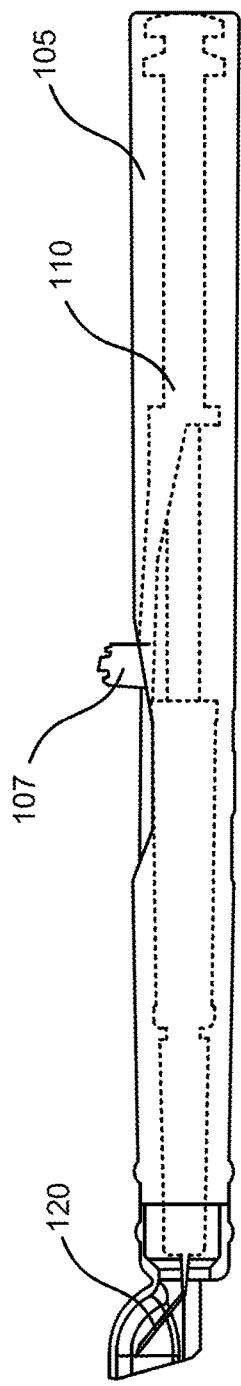
FIG. 3 shows a cross-sectional view of the blade device in the retracted state.

Before the present subject matter is further described, it is to be understood that this subject matter described herein is not limited to particular embodiments described, as such may of course vary. It is also to be understood that the terminology used herein is for the purpose of describing a particular embodiment or embodiments only, and is not intended to be limiting. Unless defined otherwise, all technical terms used herein have the same meaning as commonly understood by one skilled in the art to which this subject matter belongs.

Disclosed is a blade device, such as a medical scalpel system, that includes a safety handle and an internal mechanism that permits a blade to be extended and retracted relative to the safety handle. At least a portion of the system is manufactured pursuant to a process wherein a material, such as silicone or Teflon, is used in the manufacturing of the components to provide a smooth movement between components of the extension/retraction mechanism, as described in detail below.

FIG. 1 shows a side view of a blade device, such as a scalpel system 100, that includes an elongated handle 105 that can be grasped by a user. A control element 107, such as a knob, dial, switch, etc., is movably attached to the handle 105 and can be actuated or otherwise moved by a user to extend and retract an internal blade mechanism positioned inside the handle 105. FIG. 1 shows the system 100 in a retracted state such that the internal blade mechanism is retracted and at least partially contained within handle 105.

FIG. 2 shows the system 100 in an extended state wherein the internal blade mechanism 110 is extended such that a blade 120 protrudes outwardly from one end of the handle 105. The internal blade mechanism 110 is moved between the extended and the retracted state by actuating the control element 107, such as by sliding the control element 107 along the direction parallel to a longitudinal axis of the handle 105. The control element 107 is directly or indirectly attached to the internal blade mechanism 110 such that movement of the control element 107 results in corresponding movement of the internal blade mechanism 110.

This process is described in more detail with reference to FIG. 3 and FIG. 4. These figures show the system 100 with the handle 105 in a transparent state to show the internal mechanism 110. The handle 105 is a hollow member that defines an internal cavity that is sized and shaped to contain a complementary shaped internal mechanism 110. The control element 107 is attached or otherwise coupled to the internal mechanism 110. The control element 107 protrudes out of a side portion of the handle 105 and can be slidably positioned within a slot in the handle 105 that guides sliding movement of the control element 107.

As shown in FIG. 3, the control element 107 can be positioned at a predetermined location relative to the handle 105 such that the internal mechanism 110 and the attached blade 120 are retracted relative to the handle 105. In this regard, a shield or hood 115 can be positioned on the handle 105 such that it shields or covers the blade 120 when the system is in the retracted state.

Figure 4:
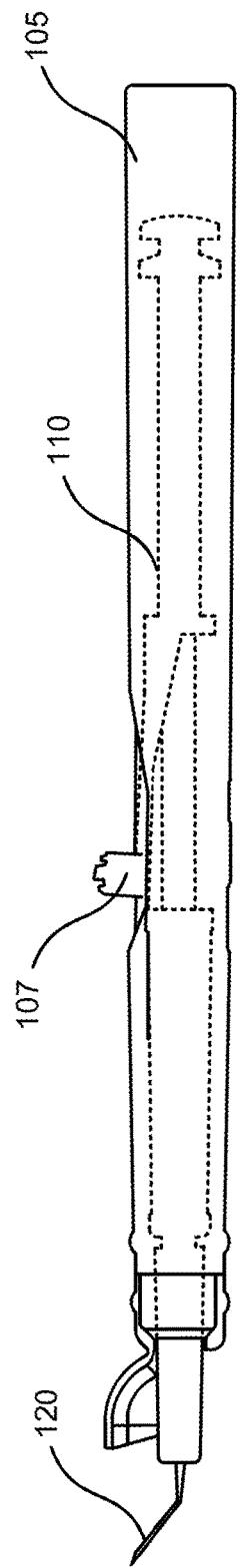
FIG. 4 shows a cross-sectional view of the blade device in the extended state.

With reference now to FIG. 4, the control element 107 moves relative to the handle 105 (such as by sliding the control element 107 in a leftward direction relative to FIG. 4). This results in corresponding movement of the internal mechanism 110 such that the blade 120 slides outward relative to the handle 1052 expose the blade 120. In this manner, with the system in the extended state shown in FIG. 4, a user can grasp the handle 105 and use the blade number 124 in a cutting procedure.

It should be appreciated that it is desirable for there to be a relatively smooth movement between the internal mechanism 110 and the handle 105 as the user actuates the control element 107 between the retracted state and the extended state, and vice versa. It is highly undesirable for there to be snagging or catching internal mechanism 110 and the handle 105 during actuation of the control element 107. In this regard, it is also desirable to minimize any friction between the moving elements of the system 107 in order to enable smooth actuation of the control element 107.

There is now described a process for manufacturing at least some of the components of the system in order to enable a smooth actuation of the control element 107. Pursuant to this process, at least a portion of the system, such as one of the handle 105, the internal mechanism 110, and the control element 107, is manufactured of moldable material, such as a plastic. At least one of these components is made pursuant to a molding process wherein a material, such as plastic is injected into a mold to form the element.

In an example, the handle 105 and the internal mechanism 110 are manufactured using a mold. A plastic resin is injected or otherwise inserted into a mold having the shape of the handle, and a plastic resin is also injected into a mold having the shape of the internal mechanism 110. A lubricant, such as silicone or Teflon, is added to the plastic resin before molding. This reduces the coefficient of friction of the resulting component formed by the mold and results in less friction as the components move relative to one another during extension and retraction of the system.

FIG. 5 shows a schematic representation of a first mold 505 having an internal cavity 510 shaped into a handle of the blade, a second mold 515 having an internal cavity 520 shaped into an internal mechanism of the handle and a lubricant 530.

In an embodiment, at least one of the components of the system is made of polysulfone, although the material may vary.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

The invention claimed is:

1. The method of manufacturing a blade device, comprising:
   providing a blade;
   injecting a first material into a first internal cavity of a first mold, wherein the first internal cavity is shaped to form a handle;
   injecting a second material into a second internal cavity of a second mold, wherein the second internal cavity is shaped to form a handle mechanism, wherein at least one of the first material and the second material includes a lubricant that reduces such material's coefficient of friction;
   permitting the first and the second material to cool within the first mold and the second mold so as to form the handle and the handle mechanism;
   assembling the handle mechanism to the handle and to the blade.

2. The method as in claim 1, wherein at least one of the first material and the second material includes thermoplastic material.

3. The method of claim 2, wherein the thermoplastic material includes polysulfone.

4. The method as in claim 1, wherein at least one of the first material and the second material is a plastic resin.

5. The method as in claim 1, wherein the lubricant is silicone or Teflon.

6. The method as in claim 1, wherein the blade is a surgical blade.

7. The method as in claim 1, wherein a portion of the handle mechanism is internal to the handle after assembling.

8. The method as in claim 7, wherein the handle mechanism includes a control element that moves the portion of the handle mechanism that is internal to the handle.

9. The method as in claim 8, wherein the control element is selected from a group consisting of a knob, a dial, and a switch.

10. The method as in claim 1, wherein the blade can retract into the handle by moving the handle mechanism after assembling.

11. The method as in claim 1, wherein the blade can extend from the handle by moving the handle mechanism after assembling.

12. The method as in claim 1, wherein a portion of the handle mechanism is external to the handle after assembling.

* * * * *